(12) United States Patent
Rossmanith

(10) Patent No.: US 6,602,416 B1
(45) Date of Patent: Aug. 5, 2003

(54) METHOD AND A DEVICE FOR THE PURIFICATION OF WASTE WATERS

(75) Inventor: Peter Rossmanith, Rielasingen-Worblingen (DE)

(73) Assignee: USF Deutschland GmbH, Fellbach (DE)

(*) Notice: Subject to any disclaimer, the term of this patent is extended or adjusted under 35 U.S.C. 154(b) by 0 days.

(21) Appl. No.: 10/019,940
(22) PCT Filed: Jul. 6, 2000
(86) PCT No.: PCT/EP00/06413
§ 371 (c)(1), (2), (4) Date: Apr. 30, 2002
(87) PCT Pub. No.: WO01/02309
PCT Pub. Date: Jan. 11, 2001

(30) Foreign Application Priority Data
Jul. 6, 1999 (DE) .......................... 199 31 085

(51) Int. Cl.⁷ .............................. C02F 3/28; C02F 11/04
(52) U.S. Cl. .................. 210/603; 210/608; 210/194
(58) Field of Search ................. 210/603, 608, 210/194, 260

(56) References Cited

U.S. PATENT DOCUMENTS

| | | | | |
|---|---|---|---|---|
| 1,690,682 A | * | 11/1928 | Imhoff et al. ............... | 210/608 |
| 2,202,772 A | * | 5/1940 | Durdin, Jr. ................... | 210/603 |
| 2,640,027 A | * | 5/1953 | McNamee et al. ........... | 210/603 |
| 2,907,712 A | * | 10/1959 | Eidsness et al. ............. | 210/208 |
| 4,609,460 A | | 9/1986 | Vellinga | |
| 4,780,207 A | * | 10/1988 | Engwirda ..................... | 210/603 |
| 5,500,118 A | * | 3/1996 | Coenen et al. ............... | 210/603 |
| 5,518,618 A | | 5/1996 | Mulder et al. | |
| 5,565,098 A | | 10/1996 | Vellinga | |
| 5,599,450 A | * | 2/1997 | Li et al. ....................... | 210/603 |
| 5,942,116 A | * | 8/1999 | Clark et al. .................. | 210/603 |
| 6,030,534 A | * | 2/2000 | De Lima ...................... | 210/629 |
| 6,309,553 B1 | * | 10/2001 | Lanting et al. ............... | 210/802 |
| 6,478,963 B1 | * | 11/2002 | Rossmanith ................. | 210/603 |

FOREIGN PATENT DOCUMENTS

EP 0 342 722 11/1989
JP 60 220194 11/1985

* cited by examiner

Primary Examiner—Fred Prince
(74) Attorney, Agent, or Firm—Young & Thompson

(57) ABSTRACT

A method and a device for purifying waste water is described, in particular for an anaerobic purification, in a container receiving a medium under the development of gas, wherein the gas developing is caught by a gas collector, ingredients of the medium entrained by the gas are separated and the ingredients separated are passed back into the medium below the gas collector. In order to improve the purification effect in a constructively simple manner, it is suggested to take in medium from the upper portion of the container by a gas lifting effect of the rising gas and to conduct it back into the container.

11 Claims, 1 Drawing Sheet

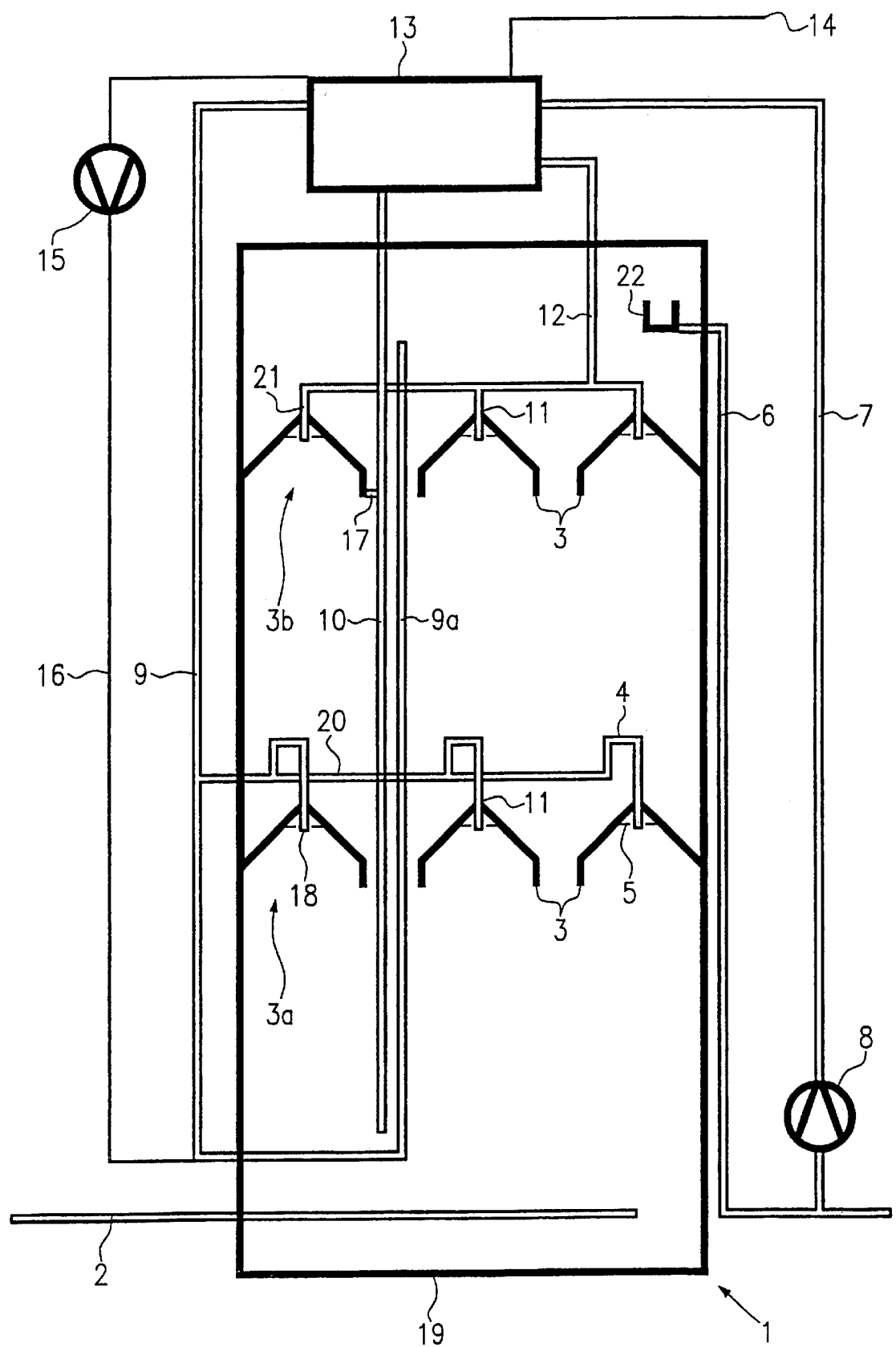

METHOD AND A DEVICE FOR THE PURIFICATION OF WASTE WATERS

FIELD OF THE INVENTION

The invention refers to a device for purifying waste water of the type described in the preamble of claim 1.

BACKGROUND OF THE INVENTION

A method of this type is known from EP 0 170 332 B1. The known device operates anaerobic, preferably according to the UASB method (upflow anaerobe sludge blanket) in which a container is used in whose lower portion the waste water to be purified is conducted and from whose upper portion the purified water is let off. Anaerobic micro organisms are active in the container. Stacked gas collectors in the form of hoods are located in the waste water inlet and the overflow for the purified water. The upper portion of the hoods is connected to a gas-sludge separation means via a line. The action of the micro organisms generates gas, which settles down on the sludge so that this sludge floats towards the top as so-called scum. This scum is caught by the hood and gradually emits its gas so that it becomes heavier and sinks back to the ground as so-called sinking sludge. The gas emitted by the pellets rises together with the free gas bubbles caught by the hoods towards the top in the lines and thereby entrains scum particles and fluid that was separated in the gas-sludge separation chamber. The gas is purposefully carried away while the fluid entrained, which may also contain sludge particles, reaches a penstock, which leads back to the bottom of the container. The purified waste water reaches a discharge line in the upper portion of the container via an overflow and is drawn off there. However, it proved that the purification power of such containers still needs to be improved.

SUMMARY OF THE INVENTION

Thus, the invention is based on the object of providing a method and a device for purifying waste water by means of which the purification effect is optimized in a constructively simple manner.

The object is solved by the features cited in claim 1. By the method according to the invention of again sucking on medium from the upper portion of the container and introducing it into the purification circle, a circulation of the medium in the container is started or enforced, which leads to a substantially improved purification effect, wherein by the utilization of the gas lifting effect of the already separated gas, this improved purification effect neither requires energy nor complicated constructive modifications for instance in already existing containers.

In a useful manner, the medium taken-in is conducted back into the container together with those ingredients of the medium that were entrained during the gas accumulation.

Claim 3 describes an especially preferred device for carrying out the method according to the invention.

To realize the improved purification effect according to the invention, only one additional line exists between the upper portion of the container and the gas collection line which can of course also easily be retrofit in already existing containers.

Advantageous embodiments of the device according to the invention can be derived from subclaims 4 to 10.

BRIEF DESCRIPTION OF THE DRAWING

An embodiment of the device according to the invention to carry out an embodiment of the method according to the invention can be derived from the enclosed only FIGURE.

FIG. 1 shows a device 1 according to the invention for the anaerobic purification of waste water according to the UASB method, which, however, is only shown schematically. The device is a development of the device that is described in the unpublished German patent application 198 15 616 to which reference is hereby made.

DETAILED DESCRIPTION OF THE INVENTION

The device 1 includes an upright standing container 19 into which a waste water line 2 opens in the bottom portion in which a sinking sludge zone provided with micro organisms is located. The waste water line may be provided with one of the conventional distributor systems for the waste water, which, however, is not shown.

A plurality of gas collectors 3 are arranged in a manner stacked across the height of the container. In the embodiment shown, the gas collectors 3 are grouped into two systems, i.e. into a lower system 3a and into an upper system 3b. Each of the gas collectors 3 is provided in the form of one of the known gas collector hoods having a downwardly pointing opening, which extends across the largest horizontal cross section of the hood and which has a vertical cross section tapering towards the top. However, different forms of gas collectors may also be used.

The gas collectors 3 of the lower system 3a of the container 19 according to the invention comprise lines 18 extending through its ridge of the roof 11 and which are welded in a gastight manner to the ridge 11. Each of the lines 18 projects from the ridge of the roof 11 a little bit further, preferably 0.1 to 0.4 times the height of the gas collector hood, downwardly into the gas collector hood and comprises a horizontal opening possibly provided with sludge repelling means. Above the ridge of the roof 11, the lines 18 have an inverted U-shaped bend 4, which is connected to a discharge line 20. The opening of the inverted U-shaped curvature 4 into the discharge line 20 or the opening of the discharge line 20 into a total collector line formed as a riser 9 is located some centimeters, preferably between 5 and 10 cm, above the opening of the line 18 below the ridge of the roof 11. The line 20, which is connected to all gas collectors 3 of the system 3a, opens into the riser 9, i.e. a pipeline having a cross section that is significantly diminished compared to the cross section of the container 19. The riser 9 leads upwardly into a gas-sludge separation means 13 arranged above the container 19. A sinking line 10 leads from this gas-sludge separation means 13 back into the container 19 and opens with a downwardly projecting, horizontal opening below the lower system 3a, and shortly above or within a sinking sludge zone formed in the container 19.

The upper system 3b of the gas collector hoods 3 usually serves for retaining scum for preventing this scum from reaching the purified waste water. The gas collectors 3 of the upper system 3b also comprise lines 21 opening upwardly over the ridge of the roof 11, however, said lines opening without the U-shaped bend 4 of the system 3a into a discharge line 12, which in turn leads into the gas-sludge separation means 13. Below the ridge of the roof 11, the lines 21 are formed as the lines 18 of system 3a.

Some or all of the gas collectors 3 of the upper system 3b may be connected to the sinking line 10 via a pipeline 16. The pipeline is located in the part of the gas collector 3 in which scum preferably collects.

Above the upper system 3b, an overflow 22 for the purified water is located which determines the water level in the container 19, said overflow opening into a water line 6.

A return line 7, which is provided with a pump 8, leads out of the water line 6 and back into the gas-sludge separation means 13. A first gas line 14 leads out of the gas-sludge separation means 13, said gas line guiding away the collected bio gas for further processing, e.g. for the generation of energy. A further gas line 16 leads out of the gas-sludge separation means 13, with a pump 15 also being connected into said gas line. The gas line 16 leads into the lower portion of the riser 9 so that the gas can be returned for supporting the lifting effect.

The riser 9 leads below the discharge line 20 with a suction line 9a into the upper portion of the container 19 and opens there below the overflow 22 for the purified water, i.e. shortly below the water level.

The device according to the invention operates according to the following method. The waste water to be purified, e.g. organically highly contaminated water from the food or paper industry, is conducted through the waste water line into the lower portion of the container 19 and into the sinking sludge layer existing there, which is provided with micro organisms, preferably in the form of conventional sludge pellets. The micro organisms decompose the organic contaminations of the waste water, which leads to the generation of gas. The gas rises in the form of gas bubbles towards the top and also gets caught on the sludge pellets, so that they become lighter and start to float. The gas and the gas-containing pellets floating in the form of scum reach the portion of the first system 3a and are caught by the gas collectors 3. The gas collects in a gas cushion 5 below the ridge of the roof 11 and above a layer formed of scum, which also gradually outputs its gas and sinks back as sinking sludge. The gas reaches the U-shaped bend 4 via the line 18. In this curvature a gas cushion is formed, which prevents rising and entraining of scum in the line 20. Thereby only the gas reaches the riser 9 via the line 20. There, the gas causes a strong, rising flow and thereby a vacuum at the intake opening of the intake line 9a. This vacuum causes medium from the upper portion of the container including the still existing ingredients, i.e. in particular substantially purified water with scum residue retained by the overflow or possibly residue gas, to be taken in and to be conducted back into the gas-sludge separation means 13 together with the entrained particles and the gas from the gas collectors. The mixture of gas, taken-in sinking sludge and water from the upper portion of the container 19 and from the portion below the gas collector is separated in the gas-sludge separation means 13, wherein the gas normally is conducted via lines 14 for further processing. The entrained sludge collects and is flushed by the water downwards via the sinking line 10 into the container 19, where it is relieved below the system 3a into the container, sinks back to the ground and causes turbulences there so that the micro organisms are rinsed by the waste water again and therefore find optimum conditions of life. Moreover, the waste water is subjected to a second cleaning process, and it is taken care that not too much residue sludge collects at the overflow 22, that there is a risk of the residue sludge being entrained into the purified water. Finally, an advantageous internal reactor circulation is generated in this manner without external energy, e.g. for a pump, having to be supplied. When the sludge sinks down from the separation means 13 through the sinking line 10, scum is taken in via the tube 17, said scum having collected below the gas collectors 3 of the upper systems 3b. This enforces the swirling effect effected by the returned sludge. A further enforcement of the swirling effect caused by the sludge sinking back may be achieved by the aid of a small quantity of waste water that is already purified, which is taken by pump 8 of the water line 6 and which is pumped back via line 7 into the separation means 13 where it helps effectively flushing out the sludge through the sinking line 10.

The intake, in particular the start of the device 1, may be supported in that gas or also air is pumped into the riser 9 via the line 16 and the pump 15.

The scum and the gas bubbles, which were not yet caught by the lower system 3a or which have exited again when the collection capacity was exceeded, reach the area of the upper system 3b and are caught by the gas collectors 3 there. The gas collecting in the ridge 11 is conducted via the straight, vertical lines 21 and the line 12 into the separation means 13, whereas the scum layer is either discharged via the tube 17 or, after outputting the gas, sinks back to the ground. The purified waste water flows into the overflow 22 and there reaches the water line 6.

If needed, the device according to the invention may also be operated additionally anaerobic, wherein oxygen at a quantity of 1 to 3 volume percent is added to the gas-sludge separation means 13 for instance to obtain a biological oxidation of the sulfur prevailing in the gas. A return of the gas via the pump 15 and the line 16 is not carried out.

Usually, anaerobic decomposition processes have an optimum between 25° C. and 37° C. By the higher flows it is possible to lower the reaction temperature. The optimum temperature for the method according to the invention is between 10 and 37° C. This means a significant saving of energy, since a heating of the waste water is no longer required.

Furthermore, the upper reactor chambers of high reactors may be provided with a higher density of pellet foam, thereby further increasing the efficiency. In the case of especially protein-containing or starch-containing waste waters, which form so-called floating coagulates, these waste waters may safely be conducted back into the ground portion.

As a modification of the embodiment described and shown, more than two gas collector systems may be provided, or the container may contain only gas collectors of the lower gas collector system if they are capable of keeping away the scum from the overflow for the purified water. In the case of particularly small reactor heights, the pump for returning the gas into the riser may operate permanently. The riser may extend in the interior of the container and the sinking line may extend outside the container. It is also possible to conduct the sinking sludge not into the separation means but via a branch line from the riser directly into the container. If it is ensured that only gas or predominantly gas reaches the riser, the gas collectors may be equipped without the U-shaped bend or with another gas-separation means, or they may be connected with such a gas-separation means connected in front of the riser. Finally, the medium taken in via the intake line, in particular if it contains few gas, or no more gas, does not have to be conducted via the separation means but it may directly reach into the container.

What is claimed is:

1. A method of purifying waste water, in particular an anaerobic purification, in a container receiving a medium under the development of gas, wherein the gas developing is caught by a gas collector, ingredients of the medium entrained by the gas are separated and the ingredients separated are passed back into the medium below the gas collector, characterized in that caused by a gas lifting effect of the rising gas, medium is taken in via an intake line from the upper portion of the container above the gas collector and is conducted back into the container.

2. A method as claimed in claim 1, characterized in that the medium taken in from the upper portion of the upper container is returned together with the ingredients separated from the gas into the lower portion of the container.

3. A device for purifying waste water, in particular by an anaerobic purification, comprising a container (19) receiving the medium, a waste water intake (2), an outtake (22) for purified water, at least one gas collector (3) arranged in the container (19) and a line (18, 4) leading upwardly from the upper portion of the gas collector, characterized in that above the gas collector (3) in the upper portion of the container (19) an orifice of an intake line (9a) is arranged, wherein the line (18) of the gas collector (3) opens into the intake line (9a) in a manner that the gas coming from the gas collector (3) can be used as a gas lifter for taking in the medium into the intake line (9a).

4. A device as claimed in claim 3, characterized in that the intake line (9a) together with the line (18) opens into a gas collector line (9), which leads into a gas-sludge separation means (13) from which a sinking line (10) leads back into the container (19) below the gas collector (3).

5. A device as claimed in claim 4, characterized in that a gas separation means (4) is provided in the gas collector (3).

6. A device as claimed in claim 5, characterized in that the gas separation means is formed of a substantially inverted U-shaped bend (4) of the line (18) upwardly leading out of the gas collector (3).

7. A device as claimed in claim 4, characterized in that a pipeline (17) from the lower portion of the gas collector (3) opens into the sinking line (10).

8. A device as claimed in claim 4, characterized in that a first system (3a) of a plurality of gas collectors (3) is provided in the container (19), said gas collectors being provided with upwardly extending lines (18) having a U-shaped bend, and that a second system (3b) of a plurality of gas collectors (3) is provided above the first system (3a).

9. A device as claimed in claim 8, characterized in that the pipeline (17) is provided between the gas collectors (3) of the second system (3b) and the sinking line (10).

10. A device as claimed in claim 3, characterized in that an additional gas line (16) opens into a riser (9).

11. A device as claimed in claim 3, characterized in that a first system (3a) of a plurality of gas collectors (3) is provided in the container (19), said gas collectors being provided with upwardly extending lines (18) having a U-shaped bend, and that a second system (3b) of a plurality of gas collectors (3) is provided above the first system (3a).

* * * * *